United States Patent [19]

McClure

[11] Patent Number: 4,563,152
[45] Date of Patent: Jan. 7, 1986

[54] COMBINATION MATRIX AND INTERPROXIMAL SANDING DEVICE

[76] Inventor: Scott G. McClure, 304 E. Mission Rd., Fallbrook, Calif. 92028

[21] Appl. No.: 691,004

[22] Filed: Jan. 14, 1985

[51] Int. Cl.⁴ .............................................. A61C 00/00
[52] U.S. Cl. ....................................... 433/39; 433/142
[58] Field of Search ................... 433/40, 39, 142, 143

[56] References Cited

U.S. PATENT DOCUMENTS 2,196,896  4/1940  Dvorak ................................. 433/39

FOREIGN PATENT DOCUMENTS 454604  2/1913  France ................................ 433/142

*Primary Examiner*—Robert Peshock
*Attorney, Agent, or Firm*—John J. Murphey

[57] ABSTRACT

A combination matrix and interproximal sanding strip for use in preparing, implanting an finishing curable dental restorations, especially of the light curable type, comprising a flexible strip having opposed sides, each side having a surface coextensive therewith, adapted for insertion between proximal tooth of the side, having a smooth surface portion on one surface for contact with the proximal surfaces surrounding the prepared cavity and the restoration material to be received therein and further having a roughened surface portion on the same side for later use in abrading and removing excess, cured restorative material that has escaped the cavity preparation, without removing the strip from interproximate the teeth.

9 Claims, 8 Drawing Figures

COMBINATION MATRIX AND INTERPROXIMAL SANDING DEVICE

BACKGROUND OF THE INVENTION

1. Field of the Invention

This invention pertains to the field of medical equipment and supplies. More particularly, it pertains to the field of dental equipment of the disposable type and, especially to strips of materials known as matrices and dental finishing and polishing devices.

2. Description of the Prior Art

Metal amalgams and foils for tooth restoration are giving way to nonmetals, such as silicates and filled and unfilled acrylic resins, when the restoration is located in the maxillary and mandibular anterior (front) teeth because of the more desirable cosmetic effect. They are also cheaper and take less time to install and are thus also desired in some posterior teeth repair. The nonmetals have poorer physicals and thus are limited to areas of low compression stress, where mastication is not a factor, such as on the proximal surfaces of maxillary lateral incisors.

Routinely, the dentist locates the carious lesion and determines the logical approach and the outline form, then gives the patient a local anesthetic, matches the color of the nonmetal material to the surrounding teeth and roughs in the outline or extension (convenience form) with the appropriate drilling instrument. The site is then isolated with a rubber dam and the cavity walls are prepared to receive the restoration material. A matrix or narrow strip of flexible material is inserted in the interproximal area to insure isolation of the site from the adjacent tooth. The cavity is then washed with an acid solution, rinsed, air dried and a thin coating of a bonding agent applied. The restoration material is then mixed in the proper proportions and inserted into the cavity. The matrix is then pulled over the proximal surface to "round off" and conform the material to the general contour of the tooth and held in place while the material cures by polymerization or other chemical reaction. Some of the modern restoration materials are cured by the incidence of light and so a high intensity light beam is directed through a diaphanous matrix and onto the injected material. It is necessary to slightly overfill the cavity with restorative material to insure absolute filling of the cavity. This excess material oozes from the cavity and forms a "flash" or overhanging lip just under the matrix that cures to a hard state.

After curing is complete, the matrix is removed and a narrow sand paper strip or polishing cloth is inserted edgewise between the teeth and reciprocated or moved back and forth by hand to abrade the overfill and remove the flash. The main problem with this procedure comes from the fact that the matrix is thinner than the sanding strip and the flash and matrix completely fill the interproximal space between the teeth. When the matrix is removed, the flash remains and there is insufficient space to allow insertion of the sanding strip with literally "prying" the teeth apart. It is common therefore that many sanding strips break while trying to insert them into the interproximal area. Sometimes, excessive force is used to insert the strip resulting in the strip being forced past the filled cavity into the gingival region near the base of the teeth causing trauma to the soft gums and hemmorage in the tissue.

SUMMARY OF THE INVENTION

This invention is a unique combination matrix and interproximal sanding device that is especially useful with nonmetallic dental restoration procedures and that overcomes the abovementioned problems in removing flash and other excessive deposits of cured material from outside the cavity preparation. The invention comprises a matrix strip having opposed sides, each side having a surface coextensive therewith; a smooth surface portion is provided on one side for isolating the lesion and pulling against the injected uncured restoration material prior to curing, and a roughened surface portion is provided on the same side to thereafter be used to abrade the flash and other excess cured material that has escaped the cavity preparation, all without removing one strip and inserting another one.

Accordingly, the main object of this invention is a device for insertion between the proximal surfaces of adjacent teeth for use in forming and conforming the surface of injected uncured restoration material to the contour of the tooth prior to and during the curing operation and thereafter for use as a sanding strip to abrade and remove the flash and other excess cured material from the mesial surface of the restored tooth so that the separate step of removing the matrix strip and inserting a new sanding strip is eliminated. Other objects include a device that conforms the uncured restorative material and abrades and polishes the cured surface thereof without the heretofore attendant problems of causing damage to the gingival region interproximate the teeth, a device that eliminates the need for a separate sanding strip, a device that eliminates the need for a plurality of sanding strips following restorative dental procedures and a device that reduces the cost of materials used in such procedures. The strip of this invention may be opaque and made of metal for use in both metallic and nonmetallic tooth restoration techniques as well.

These and other objects of the invention will become more apparent when the following Description of the Preferred Embodiment is read along with the drawings appended hereto. The scope of protection sought by the inventor may be obtained from a fair reading of the claims that conclude this specification.

DESCRIPTION OF THE PREFERRED EMBODIMENT

Figure 1:
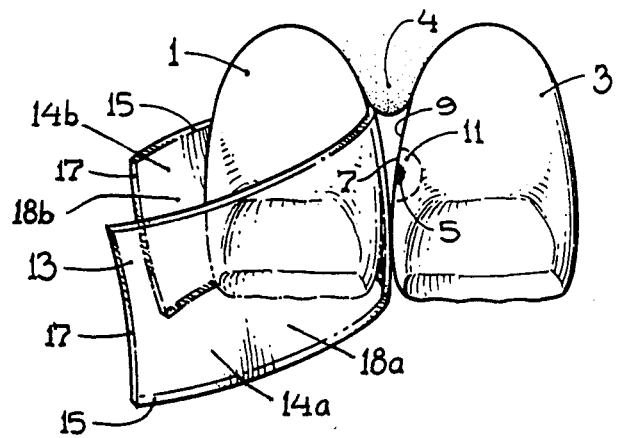
FIG. 1 shows a typical carious lesion, located on the mesial surface of a maxillary central incisor, being treated by nonmetallic restorative dental procedures utilizing the device of this invention in the interproximal area.
Figure 2:
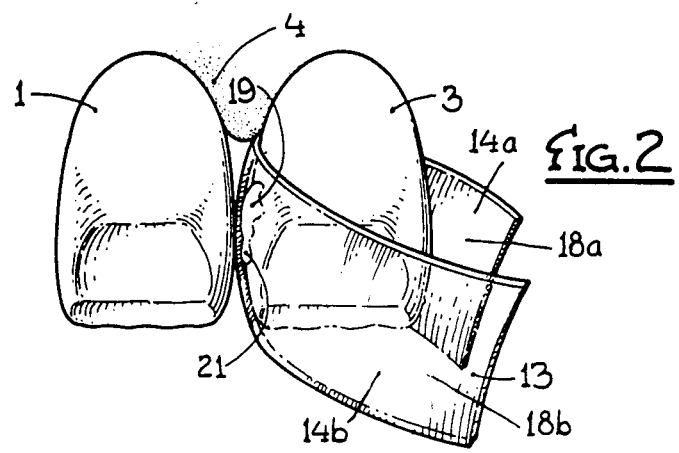
FIG. 2 is a close up of the lesioned tooth shown in FIG. 1 and shows the flash and other cured material that has escaped from the cavity preparation during the curing operation, ready for removal by the device of this invention.

FIG. 1 is a lingual view, i.e. from inside the mouth, of a pair of maxillary central incisor teeth 1 and 3 and associated gum 4 where a carious lesion site 5 is located on the mesial surface 7 of the proximal edge 9 of tooth 3. In the normal procedure, lesion 5 is opened up with a drill bit and the decayed material removed. The cavity is then extended with further drilling to a preparation or shape shown generally by dotted line 11 that is receptive to the type of restorative material to be used.

A matrix shown generally at 13, which comprises a narrow strip of nylon, Mylar (trademark) acetate or resin, about three inches in length and about ⅜ inch wide of flexible, smooth surfaced material, and having a pair of opposed sides 14a and 14b bounded by a pair of opposed edges 15 and a pair of opposed ends 17, is inserted between or interproximate teeth 1 and 3 and initially biased to the left with the fingers. Sides 14a and 14b contain surfaces 18a and 18 b respectively that are coextensive therewith. In the prior art, matrix 13 was made of either clear plastic, for primary use with nonmetallic restorations, or metal, for use with amalgam restorations.

After the cavity preparation is achieved, the site washed with an acid solution and dried and a base coating applied, an amount of soft, uncured restorative material 19 is puddled or packed therein with appropriate instruments and matrix 13 biased to the right and pulled snug over mesial surface 7 to confine the material under pressure in preparation 11 in advance of the curing step. The slight excess of material 19 oozes from preparation 11 and forms flash 21 between matrix 13 and mesial surface 7. Either self-curing or light-curing (i.e., shining a high intensity beam on material 19 through clear matrix 13) renders material 19 set and hard.

The next procedural step of removing matrix 13 from interproximate teeth 1 and 3 and inserting therein a sanding strip, to abrade and remove flash 21 and polish the exposed surface of the cured material, is reduced by this invention to merely using another portion of side 14a and its coextensive surface 18a of the same matrix to achieve abrading and polishing. FIGS. 3–8 show various embodiments of this invention to comprise a thin matrix strip 13 bounded by opposed edges 15 and opposed ends 17, as aforesaid, wherein a smooth surface portion 23 and a roughened surface portion 25 are formed on the same side 14a and make up coextensive surface 18a. Smooth surface portion 23 is useful to separate teeth 1 and 3 and for snug pulling over material 19 and roughened portion 25 is useful to abrade and remove flash and other excess cured material from mesial surface 7 and to polish the exposed surface of the cured material without removing said strip from interproximate said teeth throughout the whole restoration procedure.

Figure 3:
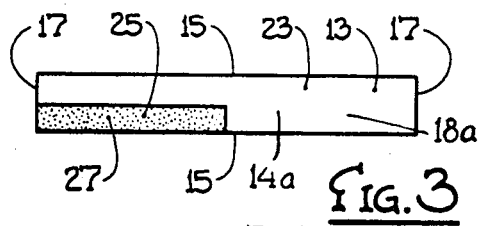
FIGS. 3–8 show various embodiments or configurations of the device of this description.
Figure 4:
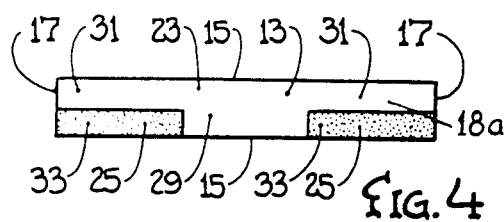
Figure 5:
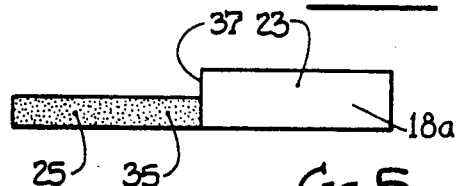
Figure 6:
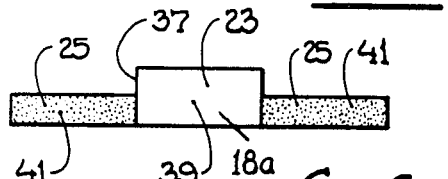
Figure 7:
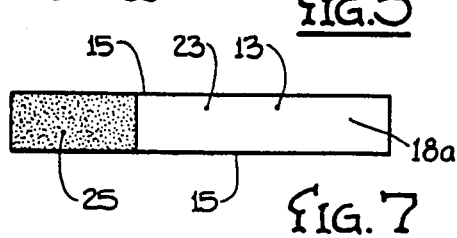
Figure 8:
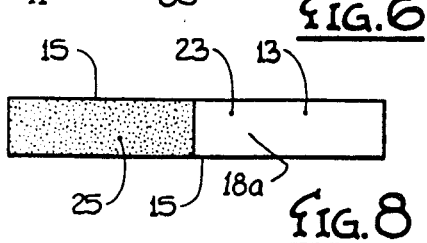

FIG. 3 shows roughened surface portion 25 to occupy a narrow, less-than-strip-wide area 27 partially along the length of strip 13. FIG. 4 shows smooth surface portion 23 to occupy a strip-wide area 29 and less-than-strip-wide areas 31 extending endwise therefrom and roughened surface portion 25 to occupy less-than-strip-wide areas 33 contiguous said less-than-strip-wide areas 31. FIG. 5 shows roughened surface portion 25 to occupy a less-than-strip-wide area 35 extending from one end 37 of strip-wide smooth surface portion 23. FIG. 6 shows smooth surface portion 23 to occupy a strip-wide area 39 intermediate less-than-strip-wide portion 41 of roughened surface portion 25 extending endwise from area 39. FIG. 7 shows smooth surface portion 23 and roughened surface portion 25 to occupy separate strip-wide areas along the length of strip 13. Said strip-wide portions may be of uneven length for some purposes. FIG. 8 shows them to be of equal length.

It is preferable that the opposite side and surface of strip 13 be kept smooth so as not to increase friction and decrease the ease of manipulation of the matrix throughout the procedure. However, there are times when a roughened surface is desired so that strips of both type are considered within the scope and spirit of this invention.

Roughened surface 18a may be imparted to matrix 13 by any conventional method such as using abrasive grit bonded to said strip with adhesives or by melting it into the plastic. The same can be said for grit imparted to metal matrices and the same are considered within the scope of this invention.

What is claimed is:

1. A combination matrix and interproximal sanding device for use in curable dental restorations comprising a flexible strip having opposed sides, each side having a surface coextensive therewith, adapted for insertion between proximal tooth surfaces, having a smooth surface portion on one said side for contact with the proximal surfaces surrounding a prepared cavity and the restoration material to be received therein and further having a roughened surface portion on the same side for later use in abrading and removing excess, cured restorative material that has escaped the cavity preparation without removing said strip from interproximate said teeth.

2. The device of claim 1 wherein said roughened surface portion occupies a narrow, less-than-strip-wide area partially along said side of said strip.

3. The device of claim 1 wherein said smooth surface protion occupies a strip-wide area and less-than-strip-wide areas extending endwise therefrom and said roughened surface portion occupies less-than-strip-wide areas of said side of said strip.

4. The device of claim 1 wherein said roughened surface portion occupies a narrow, less-than-strip-wide area extending along said side of said strip.

5. The device of claim 1 wherein said smooth suface portion occupies a strip-wide area intermediate less-than-strip-wide roughened surface portions extending endwise therefrom along said side of said strip.

6. The device of claim 1 wherein said smooth surface portion and said roughened surface portion occupy separate strip-wide areas along said side of said strip.

7. The device of claim 6 wherein said separate areas are of substantially equal length.

8. The device of claim 1 wherein said coextensive surface on said opposite side of said strip is smooth.

9. The device of claim 1 wherein said coextensive surface on said opposite side of said strip is roughened.

* * * * *